United States Patent [19]

Gratani et al.

[11] 4,373,042

[45] Feb. 8, 1983

[54] N,N-DI-(HYDROXY-PHENYL) DERIVATIVES OF PIPERAZINE AND USE THEREOF AS STABILIZERS FOR POLYMERS

[75] Inventors: Francesco Gratani, Sesto San Giovanni; Giuseppe Nelli, Milan; Piero Di Battista, San Donato Milanese; Osvaldo Cicchetti, Milan, all of Italy

[73] Assignee: Montedison S.p.A., Milan, Italy

[21] Appl. No.: 148,389

[22] Filed: May 9, 1980

[30] Foreign Application Priority Data

May 10, 1979 [IT] Italy ............................... 22515 A/79

[51] Int. Cl.$^3$ ...................... C07D 241/04; C08K 5/34
[52] U.S. Cl. ...................................... 524/100; 524/91;
524/128; 524/132; 524/222; 524/303; 524/305;
524/323; 524/328; 524/336; 524/347; 524/400
[58] Field of Search ................ 260/45.8 NH; 524/100

[56] References Cited

U.S. PATENT DOCUMENTS

| | | | |
|---|---|---|---|
| 3,435,065 | 3/1969 | Dexter et al. | 260/45.8 NH |
| 3,584,047 | 6/1971 | Dexter et al. | 260/45.8 NH |
| 3,681,358 | 8/1972 | Kleiner | 260/45.8 NH |
| 3,787,355 | 1/1974 | Linhart et al. | 260/45.8 NH |
| 4,070,338 | 1/1978 | Rosenberger et al. | 260/45.8 NH |
| 4,230,857 | 10/1980 | Drake et al. | 524/100 |

*Primary Examiner*—John Kight, III
*Assistant Examiner*—R. A. White

[57] ABSTRACT

New N,N'-di-(hydroxy-phenyl) derivatives of piperazine are disclosed. These new compounds are useful for stabilizing thermoplastic polymers, in particular polyolefins, against sunlight, heat and oxidation.

A process for producing the new compounds is also disclosed, as well as the polymeric compositions stabilized with said new compounds.

12 Claims, No Drawings

N,N-DI-(HYDROXY-PHENYL) DERIVATIVES OF PIPERAZINE AND USE THEREOF AS STABILIZERS FOR POLYMERS

THE PRIOR ART

It is known that synthetic polymers in general are subject to worsening of their physical-chemical properties when they are exposed to atmospheric agents or to heat treatments both during processing and use thereof.

It is also known, and usual, to add stabilizing substances which may be antioxidants or light stabilizers or mixtures thereof, to the synthetic polymers in order to improve their thermo- and photo-oxidative stability.

For this purpose, use is generally made of small quantities of aromatic amines, phenolic compounds, thioazolic compounds, phosphites, thiophosphites, esters, thioesters, chelates of transition metals, organo-stannic compounds, carbamates, oximes, polyquinolines and the like.

It has been recently found that also the sterically hindered aliphatic amines such as the derivatives of 2,2,6,6-tetra-alkyl-piperidine possess marked stabilizing properties.

It is known, too, that the stabilizing action of the compounds containing the sterically hindered aliphatic amines can be improved and extended by addition of phenolic groups. In such case, in fact, there is a synergistic action between the aminic and the phenolic groups.

THE PRESENT INVENTION

An object of this invention is to provide new aminic-phenolic stabilizers which exhibit remarkably improved anti-oxidizing properties.

This and other objects are accomplished by the present invention, based on our discovery that the remarkably improved anti-oxidizing agents are obtained by using the nucleus of piperazine as an aminic component of aminic-phenolic stabilizers.

The stabilizers exhibiting the improved anti-oxidizing properties are N,N-di(hydroxy-phenyl)-piperazine derivatives having the following formula (I):

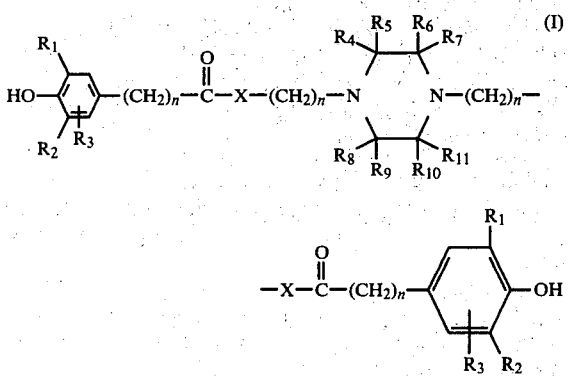

in which:
each of $R_1$ and $R_2$, which may be the same or different, is hydrogen, an alkyl radical having 1 to 8 carbon atoms, an aralkyl radical having 7 to 9 carbon atoms or a cyclo-alkyl radical having 5 to 8 carbon atoms;
$R_3$ is hydrogen or an alkyl radical having 1 to 8 carbon atoms;
each of $R_4$, $R_5$, $R_6$, $R_7$, $R_8$, $R_9$, $R_{10}$ and $R_{11}$, which may be the same or different, is hydrogen, an alkyl radical having 1 to 6 carbon atoms or $R_4$ and $R_5$, $R_6$ and $R_7$, $R_8$ and $R_9$, $R_{10}$ and $R_{11}$ together may form a cycloalkyl radical having 5 to 8 carbon atoms;

n is an integer from 1 to 12; and

X is oxygen or the group $=N-R_{12}$ in which $R_{12}$ is hydrogen, an alkyl radical having 1 to 18 carbon atoms, an alkenyl radical having 3 or 4 carbon atoms, a cycloalkyl radical having 4 to 12 carbon atoms, an aryl radical having 6 to 12 carbon atoms or an aralkyl radical having 7 to 9 carbon atoms.

The present invention provides, too, compositions based on thermoplastic synthetic polymers, stabilized to oxidation and ageing, containing, as a stabilizer, at least one of the N,N'-di-(hydroxy-phenyl)-piperazine derivatives having general formula (I) indicated hereinbefore, in an amount sufficient to prevent any degrading action.

The presently preferred N,N'-di-(hydroxy-phenyl) derivatives of piperazine having general formula (I) for use in the practice of the present invention are those in which $R_4$, $R_5$, $R_6$, $R_7$, $R_8$, $R_9$, $R_{10}$ and $R_{11}$ are each either hydrogen or methyl, $R_1$ and $R_2$ are tert.butyl, $R_3$ is hydrogen, X is oxygen and n is an integer from 2 to 6.

The N,N'-di-(hydroxy-phenyl)-piperazine derivatives of general formula (I) can be synthesized according to various methods, which consist in carrying out a series of reactions known in themselves, in different sequences.

Thus, for example, the compounds of the present invention can be synthesized by reacting a ω-hydroxy-phenyl-substituted carboxylic acid or one of its reactive derivatives, for example an ester, with N,N'-di-alkanol-piperazine or N,N'-di-alkylene-amine-piperazine, according to the following scheme:

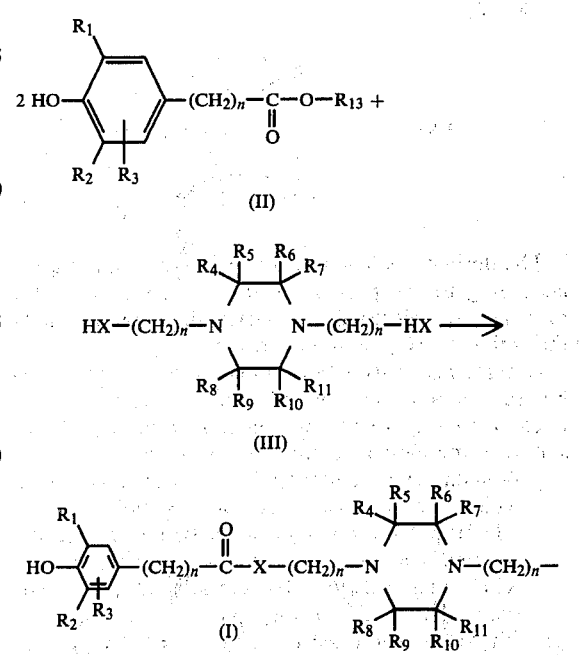

-continued

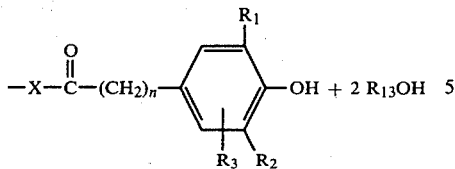

in which $R_{13}$ is hydrogen or an alkyl group containing 1 to 4 carbon atoms.

The esterification, trans-esterification or amidation reaction can be carried out in the presence of any known catalyst suitable for such reaction, such as lithium hydroxide, di-butyl-tin oxide, sodium methylate, manganese carbonate, etc.

The above-indicated product (II) can be synthesized according to any known process. Thus, for example, if n is equal to 2, the reaction schemes are as follows:

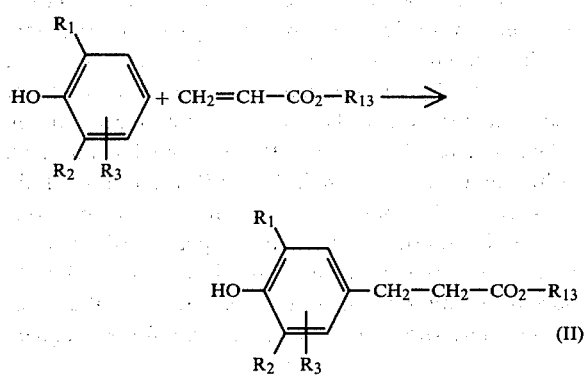

and for compound (III):

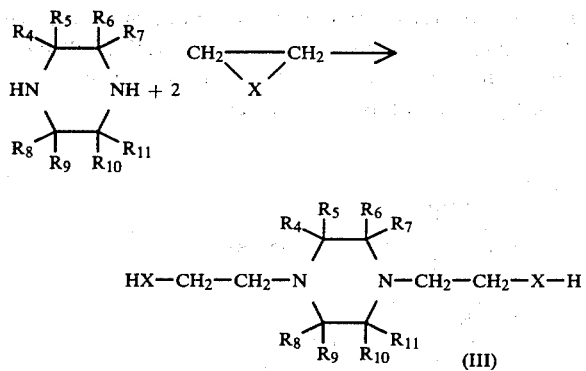

The derivatives having general formula (I) are used, according to the present invention, as stabilizers for organic materials usually subject to degradation due to the action of oxygen, light and heat.

Organic materials which can be preferably stabilized by the N,N'-di-(hydroxy-phenyl)-piperazine derivatives, according to the present invention, are all the synthetic thermoplastic polymers, including:

polyolefins, such as homopolymers of olefins, among which are high and low density polyethylene, polypropylene, polystyrene, polybutadiene, polyisoprene and the like, and copolymers of olefins with other ethylenically unsaturated monomers, such as ethylene-propylene copolymers, ethylenebutene copolymers, ethylene vinylacetate copolymers, styrene-butadiene copolymers, styrene-acrylonitrile copolymers and acrylonitrile-styrene-butadiene copolymers;

polyvinyl chloride and polyvinylidene chloride, including both the homopolymers and the copolymers of vinyl chloride and of vinylidene chloride with each other or each of them with vinyl acetate or other ethylenically unsaturated monomers;

polyacetals, such as polyoxymethylene and polyoxyethylene;

polyesters, such as polyethylene terephthalates;

polyamides, such as nylon 6, nylon 6—6 and nylon 6-10;

polyurethanes;

polycarbonates;

butadiene-styrene copolymers;

natural and synthetic rubbers, etc.

Such synthetic polymers can be used either in the form of powder or granules, or as shaped articles, such as for instance: fibers, films, sheets and other shaped articles, or as latexes and foams.

Among the above-mentioned synthetic polymers, the most suitable ones for being used according to this invention are the polyolefins deriving from monomers having the general formula: $R-CH=CH_2$, where R is an alkyl or aryl group, or a hydrogen atom.

The present preferred polyolefin is polypropylene consisting prevailingly of isotactic macromolecules and obtained by polymerization of propylene in the presence of stereospecific catalyst.

The amount of N,N'-di-(hydroxy-phenyl) derivatives of piperazine, having general formula (I), to be added to the synthetic thermoplastic polymers to be stabilized, according to this invention, is not critical and may vary over a wide range as a function of the type, properties and particular uses of the polymer. Generally, said derivatives can be added to the polymers in amounts ranging from 0.01 to 5.0% by weight, based on the polymer weight; in practice, however, the effective amount varies as a function of the type of polymer to be stabilized. Thus, for instance, in the case of polyolefins, an effective amount can range from 0.01 to 2% by weight; in the case of polyvinyl chloride and of polyvinylidene chloride such amount may range from 0.01 to 1% by weight, while for polyurethanes and polyamides such amount may vary from 0.01 to 5% by weight.

The stabilizer having general formula (I) can be employed either alone or in admixture with other known additives such as antioxidants, ultraviolet ray absorbers, pigments, fillers, basic nitrogen-containing polycondensates, other stabilizers, etc. Some examples of such additives are oxy-benzo-triazoles, oxy-benzo-phenones, Ni-stabilizers, metal soaps, phenolic antioxidants, phosphites, thioesters, hydroquinone derivatives, triazine compounds, acrylamine-phenols, benzyl-phosphonates, etc.

Such additives can be used together with N,N'-di-(hydroxy-phenyl)-piperazine derivatives having general formula (I), according to this invention, in a ratio by weight ranging between 0.5:1 and 3:1.

The incorporation of the derivatives having general formula (I) or of the mixture containing said compounds, into the synthetic polymer may be carried out according to any conventional procedure and at any stage prior to or during the manufacturing of the shaped article from the polymer. For example, it is possible to effect a simple admixing, under stirring, of the additives in powder form to the polymer, or the polymer can be mixed with a solution of the stabilizers in a suitable solvent, which is then evaporated; or the stabilizers can be added to the polymer at the end of the polymerization.

Furthermore it is possible to attain the stabilizing action by applying the stabilizer to the manufactured article, for instance by dipping it into a solution or a dispersion of the stabilizer and by successively evaporating the solvent or the dispersant.

The following non-limiting examples are given for a more detailed understanding of the present invention and for further enabling those skilled in the art to practice the same.

Unless otherwise specified, all the parts in the examples are in parts by weight.

EXAMPLE 1

Preparation of di-$\beta$-(3,5-di-tert.butyl-4-hydroxy-phenyl)-propionate of (N,N'-diethyl)-2,5-di-methyl-piperazine 16 g (0.08 moles) of N,N'-bis-(2-hydroxyethyl)-2,5-dimethyl-piperazine, 51 g (0.175 moles) of 3,5-di-tert.butyl-4-hydroxy-phenyl propionate of methyl and 0.8 g of anhydrous lithium hydroxide, as a catalyst, were introduced into a 100 cc flask equipped with a stirrer, a heating sleeve and a thermometer, and connected with a vacuum pump.

The mixture, under stirring, was heated to 110° C. and maintained at such temperature for 4 hours under a residual pressure of 20 mm of Hg. The methanol resulting from the reaction was removed by evaporation.

The reaction product, after cooling, was dissolved in methylene chloride and repeatedly washed with water. After evaporation of the methylene chloride, a raw yellow-red product was obtained, which was crystallized from ethanol and hexane. A white product in the form of a crystalline powder, having a melting point of 116° C. was so obtained.

The elemental analysis of the obtained product gave the following results:

C = 73.06%
H = 9.73%
N = 3.85%.

On the basis of the elemental analysis and of the nuclear magnetic resonance (N.M.R.) spectrum, to the product was attributed the following structural formula:

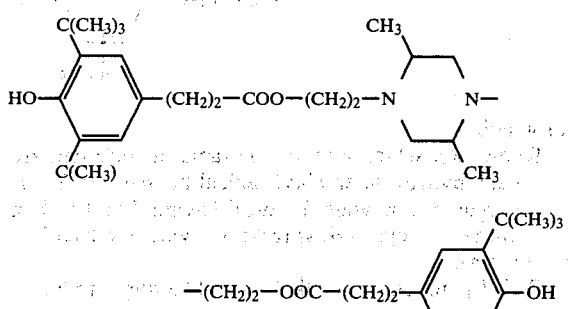

having the following calculated elemental composition:
C = 73.09%
H = 9.75%
N = 3.87%.

STABILIZATION TESTS 200 cc of chloroform containing, dissolved therein, di-$\beta$-(3,5-di-tert.butyl-4-hydroxy-phenyl)-propionate of (N,N'-diethyl)-2,5-di-methyl-piperazine, as prepared in Example 1 and in amounts as indicated in Table I, were added to 300 g of non-stabilized polypropylene, having an intrinsic viscosity, determined at 130° C. in tetralin, of 162 cc/g, a residue after the extraction of the crude polymerizate with heptane of 96.5% and an ashes content of 80 ppm.

The mixture was stirred for about 6 hours at room temperature in a rotary evaporating apparatus, whereupon it was dried at 0.01 mm of Hg and at 50° C. for 1 hour. The additioned powder so obtained was extruded in a Brabender extruder at 220° C. and granulated. The granules were then molded to films and small plates at 200° C. for 3 minutes by compression between two square steel plates measuring 20 cm × 20 cm, under a load of 1000 kg. The films so obtained had a uniform thickness of 50-60 microns and the plates a thickness of 1 mm and were practically colorless and homogeneous.

The thermal-oxidative stability was determined on the specimens so obtained. As thermal-oxidative stability value the following was assumed:

(a) the induction period (Ip) of the thermo-oxidation at 170° C. and 760 mm of Hg of oxygen, considered as the time required for getting a quick increase of the oxygen absorption rate; and (b) the resistance to ageing in oven, intended as the time (T.I.) required to evidence at naked eye, on the examined small plate, any cracks or chalking of the surface or other modifications, after exposure of the test piece in an oven at 150° C. in an air stream.

To determine the induction period of the thermo-oxidation, 0.2 g of the above film were cut into pieces and introduced into a cell of about 50 cm³, in which an oxygen atmosphere was created by repeatedly removing and introducing oxygen. The cell was connected with an oxygen absorption measuring device, equipped with recording systems of the absorbed volumes. The cell was dipped into a thermostatic bath maintained at a temperature of 170° C. The values of the induction period (Ip) and of the embrittlement time (T.I.) are recorded in the following Table I.

TABLE I

| Stabilizer | Thermo-oxidative stability | |
|---|---|---|
| % by weight | Ip in hours | Embrittling time (T.I.) in hours |
| — | 0 | 24 |
| 0.25 | 18 | 600 |
| 0.50 | 52 | 800 |
| 0.75 | >60 | 1050 |

EXAMPLE 2

Preparation of di-$\beta$-(3,5-di-tert.butyl-4-hydroxy-phenyl) propionate of (N,N'-diethyl)-piperazine By operating according to Example 1, 15 g of N,N'-bis-(2-hydroxyethyl)-piperazine were reacted with 50 g of 3,5-di-tert.butyl-4-hydroxy-phenyl-propionate of methyl. The product obtained was in the form of a white powder having a melting point of 135°–136° C.

The elemental analysis of the product gave the following results:
C = 72.57%
H = 9.57%
N = 4.00%.

On the basis of the elemental analysis and of the N.M.R. spectrum, the following structure was attributed to the obtained product:

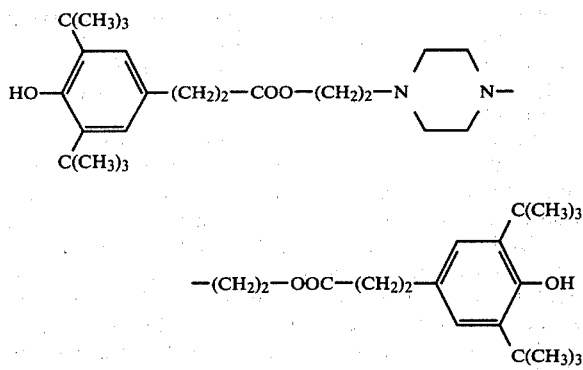

the theoretical elemental composition thereof being as follows:
C=72.58%
H=9.57%
N=4.02%.

STABILIZATION TESTS

By operating according to Example 1, specimens having the above-mentioned dimensions were prepared. The specimens were subjected to the thermo-oxidative stability tests, as in Example 1, and the obtained results are recorded in Table II.

TABLE II

| Stabilizer % by weight | Thermo-oxidative stability | |
|---|---|---|
| | Ip in hours | Embrittling time (T.I.) in hours |
| 0.25 | 6.0 | 250 |
| 0.50 | 19.1 | 600 |
| 0.75 | 26 | 840 |

EXAMPLE 3

Preparation of di-β-(3,5-di-tert.butyl-4-hydroxy-phenyl) propionate of (N,N'-diethyl)-2,2,5,5-tetramethyl-piperazine By operating according to Example 1, 3.45 g of N,N'-bis-(2-hydroxyethyl)-2,2,5,5-tetramethyl-piperazine were reacted with 8.76 g of 3,5-di-tert.butyl-4-hydroxy-phenyl propionate of methyl. 9.5 g of product in the form of a white powder, having a melting point of 95°–96° C., were obtained.

The elemental analysis of the product gave the following results:
C=73.60%
H=9.92%
N=3.70%.

On the basis of the elemental analysis and of the N.M.R. spectrum, the following structural formula was attributed to the product:

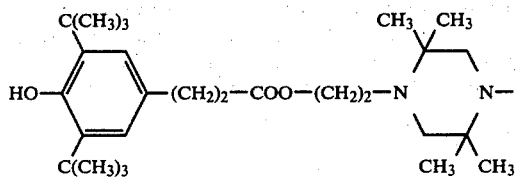

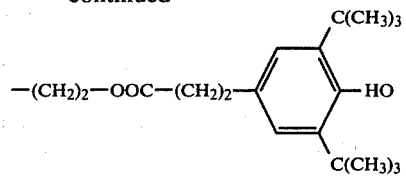

the theoretical elemental composition being the following:
C=73.56%
H=9.93%
N=3.73%.

STABILIZATION TESTS

By operating according to Example 1, some specimens having the dimensions indicated hereinbefore were prepared. The specimens were subjected to the thermo-oxidative stability tests, as in Example 1; the results obtained are recorded in the following Table III.

TABLE III

| Stabilizer % by weight | Thermo-oxidative stability | |
|---|---|---|
| | Ip in hours | Embrittling time (T.I.) in hours |
| 0.25 | 27 | 850 |
| 0.50 | >60 | 1150 |
| 0.75 | >60 | 1400 |

What we claim is:

1. A composition comprising a thermo-plastic synthetic polymer, stabilized to oxidation, to heat and to sunlight, said composition containing incorporated therein, in an amount sufficient to prevent any degradation of the polymer, a N,N'-di-(hydroxy-phenyl) derivative of piperazine having the following formula (I):

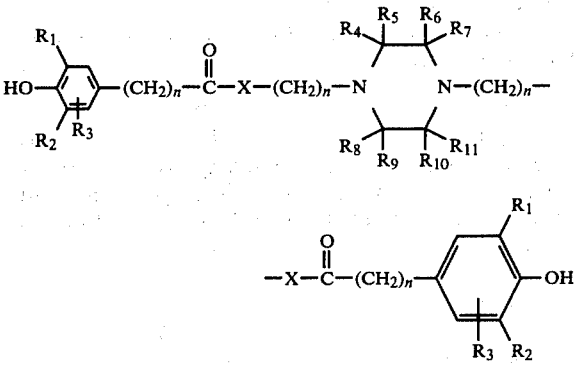

in which:
$R_1$ and $R_2$, which may be the same or different, are each hydrogen, an alkyl radical having 1 to 8 carbon atoms, an aralkyl radical having 7 to 9 carbon atoms or a cyclo-alkyl radical having 5 to 8 carbon atoms;
$R_3$ is hydrogen or an alkyl radical having 1 to 8 carbon atoms;
$R_4$, $R_5$, $R_6$, $R_7$, $R_8$, $R_9$, $R_{10}$ and $R_{11}$, which may be the same or different are each hydrogen or an alkyl radical having 1 to 6 carbon atoms, at least two thereof being different from hydrogen, or $R_4$ and $R_5$, $R_6$ and $R_7$, $R_8$ and $R_9$, $R_{10}$ and $R_{11}$ together can form a cycloalkyl radical having 5 to 8 carbon atoms;
n is an integer from 1 to 12; and X is oxygen.

2. A composition according to claim 1, in which the N,N'-di-(hydroxy-phenyl) derivative of piperazine has general formula (I) in which each of $R_4$, $R_5$, $R_6$, $R_7$, $R_8$, $R_9$, $R_{10}$ and $R_{11}$ is hydrogen or methyl, at least two thereof being methyl, each of $R_1$ and $R_2$ is tert.butyl, $R_3$ is hydrogen, X is oxygen and n is an integer from 2 to 6.

3. A composition comprising thermoplastic synthetic polymers, stabilized to oxidation, to heat and to sunlight, said composition containing incorporated therein, in an amount sufficient to prevent any degradation of the polymer, a N,N'-di-(hydroxy-phenyl) derivative of piperazine having the following formula (I):

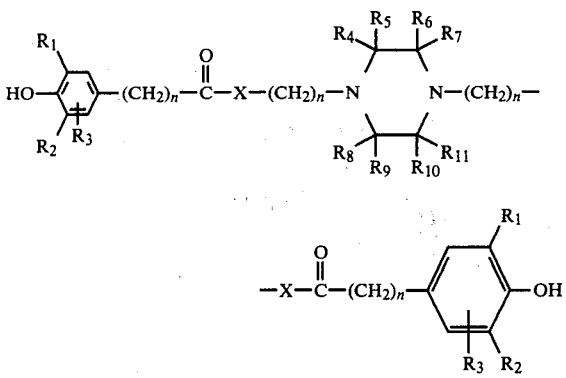

in which:
- $R_1$ and $R_2$, which may be the same or different, are each hydrogen, an alkyl radical having 1 to 8 carbon atoms, an aralkyl radical having 7 to 9 carbon atoms or a cyclo-alkyl radical having 5 to 8 carbon atoms;
- $R_3$ is hydrogen or an alkyl radical having 1 to 8 carbon atoms;
- $R_4$, $R_5$, $R_6$, $R_7$, $R_8$, $R_9$, $R_{10}$ and $R_{11}$, which may be the same or different are each hydrogen or an alkyl radical having 1 to 6 carbon atoms, at least one thereof being different from hydrogen, or $R_4$ and $R_5$, $R_6$ and $R_7$, $R_8$ and $R_9$, $R_{10}$ and $R_{11}$ together can form a cycloalkyl radical having 5 to 8 carbon atoms;
- n is an integer from 1 to 12; and
- X is oxygen or the group $=N-R_{12}$ in which $R_{12}$ is hydrogen, an alkyl radical having 1 to 18 carbon atoms, an alkenyl radical having 3 or 4 carbon atoms, a cycloalkyl radical having 4 to 12 carbon atoms, an aryl radical having 6 to 12 carbon atoms or an aralkyl radical having 7 to 9 carbon atoms.

4. A composition according to claim 1, in which the thermoplastic synthetic polymer is a polyolefin.

5. A composition according to claim 4, in which the polyolefin is polypropylene consisting prevailingly of isotactic macromolecules.

6. A composition according to claim 4, in which the N,N'-di-(hydroxy-phenyl) derivative of piperazine having general formula (I) is present in an amount of from 0.01 to 2% by weight on the weight of the polyolefin.

7. A composition according to claim 1, in which the thermoplastic synthetic polymer is polyvinyl chloride or polyvinylidene chloride.

8. A composition according to claim 7, in which an N,N'-di-(hydroxy-phenyl) derivative of piperazine having general formula (I) is present in an amount of from 0.01 to 1% by weight referred to the polymer weight.

9. A composition according to claim 1, in which the thermoplastic synthetic polymer is a polyurethane or a polyamide.

10. A composition according to claim 9, in which an N,N'-di-(hydroxy-phenyl) derivative of piperazine having general formula (I) is present in an amount of from 0.01 to 5% by weight referred to the polymer weight.

11. Compositions according to claim 1, in which the compound of formula I is employed in admixture with at least one additive selected from the group consisting of oxy-benzotriazols, oxy-benzo-phenones, Ni stabilizers, metal soaps, phenolic antioxidants, phosphites, thioesters, hydroquinone derivatives, triazines, acyl-aminophenols and benzylphosphonates.

12. A composition according to claim 11, in which the ratio by weight of the other additive to the N,N'-di-(hydroxyphenyl) derivative of piperazine having general formula (I) is from 0.5:1 to 3:1.

* * * * *